(12) United States Patent
Modi

(10) Patent No.: US 8,623,401 B2
(45) Date of Patent: Jan. 7, 2014

(54) WAFER FORMULATION

(75) Inventor: Pankaj Modi, Ancaster (CA)

(73) Assignee: Fenwafe Inc., Nepean, Ontario (CA)

( * ) Notice: Subject to any disclaimer, the term of this patent is extended or adjusted under 35 U.S.C. 154(b) by 1151 days.

(21) Appl. No.: 12/078,092

(22) Filed: Mar. 27, 2008

(65) Prior Publication Data

US 2009/0246257 A1    Oct. 1, 2009

(51) Int. Cl.
*A61K 9/28* (2006.01)
*A61K 9/00* (2006.01)
*A61K 9/70* (2006.01)
*A61K 31/439* (2006.01)

(52) U.S. Cl.
CPC ............ *A61K 9/0056* (2013.01); *A61K 9/7007* (2013.01); *A61K 31/439* (2013.01)
USPC ....................................... 424/441

(58) Field of Classification Search
USPC .......... 424/434, 435, 441, 443, 484; 514/777, 514/782; 264/160, 489
See application file for complete search history.

(56) References Cited

U.S. PATENT DOCUMENTS

| | | | | |
|---|---|---|---|---|
| 4,673,679 A * | 6/1987 | Aungst et al. | ................ | 514/282 |
| 2003/0035831 A1 * | 2/2003 | Modi | .................. | 424/465 |
| 2003/0224044 A1 * | 12/2003 | Weibel | .................. | 424/465 |
| 2007/0281003 A1 * | 12/2007 | Fuisz et al. | .................. | 424/443 |
| 2008/0050422 A1 * | 2/2008 | Myers et al. | ................ | 424/439 |
| 2008/0220029 A1 * | 9/2008 | Ng et al. | .................. | 424/401 |

FOREIGN PATENT DOCUMENTS

| | | |
|---|---|---|
| CA | 2414665 | 1/2003 |
| CA | 2472967 | 8/2003 |
| CA | 2493786 | 2/2004 |
| EP | 1897543 | 3/2008 |

OTHER PUBLICATIONS

Poklis, A. "Fentanyl: A Review for Clinical and Analytical Toxicologists", Clinical Tocicology, 33(5), 439-447 (1995).*
Streissand, James B., Vavrel, John R., Stanski, Donald R., Maire, Leon Le., Asburn, Michael A., Hague, Brian I., Traver, Stphen R.; "Absorption and Bioavailability of Oral Transmucosal Fentanyl Citrate"; Anesthesiology, 75:223-229 (1991).*
Streissand, James B., Busch, Michael A., Egan, Talmage E., Smith, Barbara Gaylord, Gay, Mason, and Pace, Nathan L.; "Dose Proportionality and Pharmacokinetics of Oral Transmucoscal Fentanyl Citrate", Anesthesiology, V 88 No. 2 p. 305-09 Feb. 1998.*

* cited by examiner

*Primary Examiner* — Brian Gulledge

(57) ABSTRACT

An orally administrable wafer is provided comprising at least one physiologically acceptable film forming agent. The wafer is formed by mixing the film-forming agent with an aqueous solution to form a gel and exposing the gel to a plurality of heating and cooling cycles. The wafer is rapidly dissolving and suitable for administration of pharmaceutical agents.

13 Claims, 1 Drawing Sheet

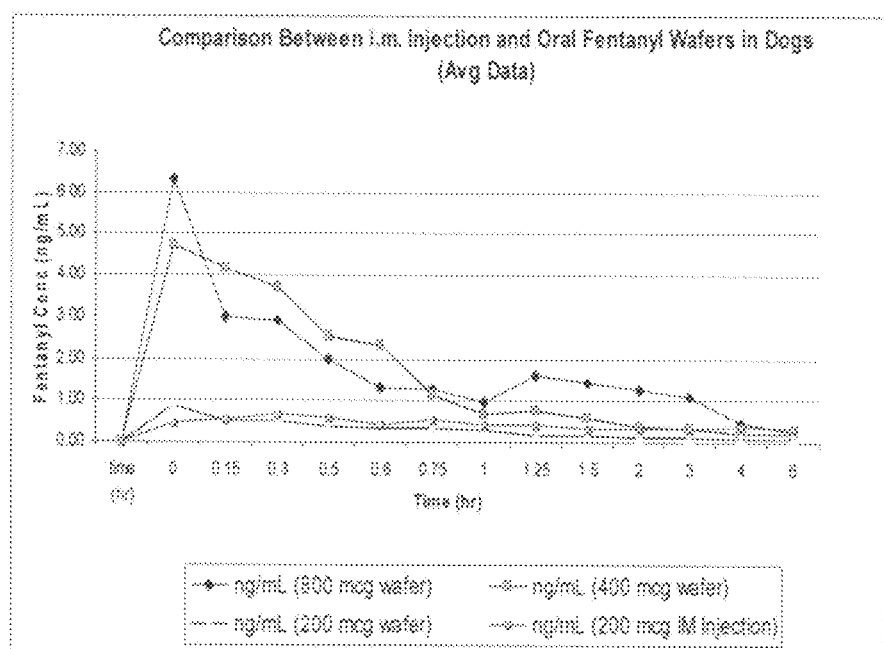

WAFER FORMULATION

FIELD OF INVENTION

The present invention relates to a wafer formulation, and in particular, it relates to a rapidly dissolving formulation suitable for oral administration.

BACKGROUND OF THE INVENTION

Medical efforts to treat pain, known as "pain management", address a large market, as clinical pain is a worldwide problem with serious health and economic consequences. For example, in the United States, medical economists estimate that the effects of pain result in approximately $100 billion (USD) in costs annually, including an estimated $515 million (USD) in lost work days. According to the National Institute of Health, approximately 40 million Americans are unable to find relief from their pain. This includes approximately one million cancer patients that suffer from severe pain at any given time, and an estimated 10% of the more than 200,000 AIDS patients that suffer severe pain.

Drugs are a key element in the treatment of pain. The worldwide market for pain was about $40.7 billion in 2004. The pain management market has grown immensely in recent years and is expected to continue to grow significantly. The pain management market has grown by more than 34% per year during the past five years. This is likely due to a number of factors, such as, a rapidly aging population, patient demand for rapid effective pain relief, increasing recognition of the therapeutic and economic benefits of rapid and effective pain management by physicians, healthcare providers and payers, and longer survival times for patients with painful chronic conditions, such as cancer and AIDS.

Many different kinds of pain exist including acute, chronic, persistent and breakthrough pain. As well, there exist different approaches to treat pain. Opioids are typically prescribed to manage moderate-to-severe acute or chronic breakthrough pain due to the fact that fast-acting, short-lived opioids can provide rapid delivery. The most common acute use of opioids is for post-surgical pain. Opioid drugs used to treat acute pain include intravenous fentanyl, hydrocodone and oral oxycodone, which provide rapid pain relief. Intravenous therapy, however, is expensive and is suitable for hospitalized patients only.

The route of administration of any medication is an important consideration. Although many patients prefer oral administration of medications, oral medication is not always "fast-acting", a property which is clearly desirable in the treatment of acute breakthrough pain, for example. Also, orally administrable medications are generally provided in the form of solid shaped articles such as tablets, pills, caplets and capsules that retain their shape under moderate pressure. Some patients, particularly pediatric and geriatric patients, have difficulty administering an oral medication due to inability to swallow, nausea or other gastrointestinal problems. Breakthrough pain medications can be taken in other ways, including by injection, under the tongue (sublingual), rectally, or transmucosally absorbed in the mouth but not swallowed; however, these forms of administration are often not as "fast-acting" as would be desired.

Liquid, syrups or suspensions are an alternative to solid dosage forms and are often preferred for pediatric and geriatric patients who have problems swallowing tablets. However, these dosage forms can be difficult to measure accurately and administer easily. Liquid formulations often deteriorate rapidly upon exposure to heat or other atmospheric conditions and consequently have a relatively short shelf life. Furthermore, liquid formulations require a relatively large volume and are bulky to store.

The bitter after-taste of many drugs which are orally administered, such as tablets, capsules or suspensions, often contributes to patient non-compliance in taking medicine. Apart from the taste of a chewable nutritional supplement, the 'mouth-feel' of the supplement must also be taken into account. 'Mouth-feel' is a concept that encompasses non-taste-related aspects of the sensation experienced by a person while chewing or swallowing a nutritional supplement. Aspects of mouth-feel include, for example, the hardness and brittleness of a composition, whether the composition is chewy, gritty, oily, creamy, watery, sticky, easily dissolved, astringent, effervescent, and the like, and the size, shape, and form (tablet, powder, gel, etc.) of the composition.

In view of the foregoing, there remains a need to develop a formulation for the oral delivery of a pharmaceutical agent that overcomes at least one of the disadvantages of prior formulations.

SUMMARY OF THE INVENTION

The present invention provides a novel orally administrable and rapidly dissolving wafer. The wafer is advantageously stable but readily dissolves on oral administration. Accordingly, the wafer is suitable for the oral administration of a compound such as a pharmaceutical agent to permit rapid release and onset of activity of the compound incorporated within the wafer.

Thus, in one aspect of the present invention, there is provided an orally administrable wafer comprising at least one physiologically acceptable film forming agent and an aqueous solvent, wherein said wafer is characterized by a dissolution rate of at least about 2 mg/s in an aqueous environment.

In another aspect of the invention, an orally administrable wafer is provided, comprising at least one physiologically acceptable film forming agent, wherein said wafer is formed by exposing an aqueous mixture of the film forming agent to a plurality of heating and cooling cycles.

In another aspect of the present invention, there is provided an orally administrable wafer comprising an aqueous mixture of a pharmaceutical agent and at least one physiologically acceptable film forming agent, wherein the wafer is formed by exposing the mixture to a plurality of heating and cooling cycles.

In another aspect of the present invention, there is provided an orally administrable wafer comprising a pharmaceutical agent and at least one physiologically acceptable film forming agent, wherein the pharmaceutical agent is present in a pre-defined quantity.

In another aspect, there is provided a method of preparing an orally administrable wafer. The method comprises the steps of:
1) mixing at least one physiologically acceptable film forming agent with an aqueous solution to form a gel; and
2) exposing the gel to cycles of heating and cooling to transform the gel mixture into a wafer.

In a further aspect of the present invention, there is provided a method of administering a pharmaceutical agent to a mammal comprising the step of orally administering to the mammal a wafer comprising the pharmaceutical agent, wherein said wafer comprises at least one physiologically acceptable film forming agent and the pharmaceutical agent and is characterized by a dissolution rate of at least about 2 mg/s in an aqueous environment.

These and other aspects of the invention will become apparent in the detailed description and drawings in which:

BRIEF DESCRIPTION OF THE DRAWINGS

FIG. 1 graphically compares blood levels of fentanyl when administered to a mammal by injection and orally in a wafer in accordance with an aspect of the invention.

DETAILED DESCRIPTION

An orally administrable wafer is provided comprising at least one physiologically acceptable film forming agent. The wafer is formed by exposing an aqueous mixture of the film forming agent to a plurality of heating and cooling cycles to result in a wafer product having a very rapid rate of dissolution in an aqueous environment.

An orally administrable wafer according to the present invention may be made using one or more physiologically acceptable film forming agents. The term "physiologically acceptable" is used herein to refer to film-forming agents that are acceptable for consumption by a mammal and that exhibit minimal or no adverse side effects on consumption. Suitable film-forming agents for use to make the wafer include, for example, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, polyacrylic acid, glycolide, polylactide, methylmethacrylate copolymer, carboxyvinyl polymer, amylose, high amylose starch, hydroxypropylated high amylose starch, dextrin, pectin, chitin, chitosan, levan, elsinan and mixtures thereof. A preferred film forming agent is pullulan, in amounts ranging from about 0.01 to about 99 wt %, preferably from about 30 to about 80 wt %, more preferably from about 45 to about 70 wt % of the film and even more preferably from about 60 to about 65 wt % of the film. Another preferred film forming agent is a mixture of pullulan, PEG and poly vinyl alcohol and carrageenan, each in amounts ranging from about 0.01 to about 95 wt % of the film.

Secondary film forming agents may be added to the formulation to optimize wafer characteristics such as tensile strength, stability, flexibility and brittleness including agents such xanthan gum, tragacanth gum, guar gum, acacia gum, arabic gum, collagen, gelatin, zein, gluten, soy protein isolate, whey protein isolate, casein and mixtures thereof. The amount of secondary film forming agent will vary depending on the primary film forming agent used as well as the desired properties of the wafer.

The one or more selected film-forming agents are dissolved in an aqueous solution to form a gel. The aqueous solution may simply be water, or a water-based solution such as mixtures of water and ethyl alcohol. One of skill in the art will be familiar with the amounts of aqueous solution to add to a film-forming agent to form a gel. Generally, a gel is formed by mixing a 4:1 ratio of film forming agent to aqueous solution. One of skill in the art will appreciate that this may vary with the selected film forming agent and aqueous solution.

To form the wafer, a novel method is employed comprising exposing the gel to a plurality of heating and cooling cycles. Thus, the gel is exposed to a period of heating in which the gel is rapidly heated to a temperature of up to about 90° C., for example a temperature of between about 60-80° C., for a period of time of not more than about 20 s, for example 5-15 s, and preferably 8-12 s. Following the heating period, the gel is exposed to a cooling or non-heating period for a period of time of not more than about 20 s, for example 5-15 s, and preferably 8-12 s. This cycle is repeated a number of times to yield a wafer in accordance with the present invention, for example, the gel is exposed to at least 3 cycles of heating and cooling in which the total time is between about 30 s-3 minutes, preferably about 1-2 minutes. Preferably, the method of making the wafer comprises at least about 6 heating and cooling cycles.

The present method, thus, provides a means of rapidly preparing a dissolvable wafer product, e.g. a preparation time of minutes, as opposed to the conventional batch extrusion method of preparing films which can take hours to yield a product.

Although the method of heating the gel during the heating period is not to be restricted, the application of microwaves is particularly suitable since microwaves are suitable to achieve rapid high temperature heating of the gel. The application of microwaves may be by a mono-mode or multi-mode structure. Typically the wavelength of the microwave radiation is chosen so as to excite the solvent molecules, especially water, and expedite their evaporation. A standard microwave oven, designed to use 1,100 W AC and producing 700 W of microwave power, emitting microwaves at a frequency of 2.45 GHz and a wavelength of 12.24 cm, is suitable to heat the gel during the heating period of the present method.

The result of the multiple heating and cooling cycles on the gel is a wafer having unique morphological characteristics that confer on it a very high rate of dissolution that exceeds the dissolution rate of other film-like formulations. The wafer is thus characterized by a dissolution rate of at least about 2 mg/s, for example 3-5 mg/s. The rapid dissolution rate of the wafer results in very rapid absorption of the components thereof, through the buccal mucosa, rendering the wafer particularly suitable as a means to orally deliver a pharmaceutical agent. Thus, the wafer exhibits maximum or peak absorption of a component therein within about 5-10 minutes ($T_{max}$), for example, within about 5-7 minutes which is at least comparable or less than the absorption time for a component administered intravenously.

In addition, the maximum plasma concentration ($C_{max}$) of a component administered to a patient via the wafer is increased in comparison to the $C_{max}$ of the component when administered intravenously. Notably, the $C_{max}$ attained on administration of a component via a wafer according to the invention is at least about 25% greater, preferably at least about 30-40% greater and more preferably, at least about 50% greater than the $C_{max}$ attained on administration of the component to a patient intravenously.

The present method advantageously yields a wafer product that is extremely thin, exhibiting a thickness of no more than about 0.1 mm, for example, 0.05 mm or less. This property of the wafer contributes to its rapid dissolution, and ease of administration.

In another aspect, thus, of the invention, an orally administrable wafer formulation comprising a pharmaceutical agent and at least one physiologically acceptable film forming agent is provided.

As used herein, the term "pharmaceutical agent" is meant to refer to any compound useful to treat or reduce the symptoms of a medical condition. Examples of pharmaceutical agents include, but are not limited to:

a. antimicrobial agents, such as triclosan, cetyl pyridium chloride, domiphen bromide, quaternary ammonium salts, zinc compounds, sanguinarine, fluorides, alexidine, octonidine, EDTA, and the like;

b. non-steroidal anti-inflammatory drugs, such as aspirin, acetaminophen, ibuprofen, ketoprofen, diflunisal, fenoprofen calcium, naproxen, tolmetin sodium, indomethacin, and the like;
c. anti-tussives, such as benzonatate, caramiphen edisylate, menthol, dextromethorphan hydrobromide, chlophedianol hydrochloride, and the like;
d. decongestants, such as pseudoephedrine hydrochloride, phenylepherine, phenylpropanolamine, pseudoephedrine sulfate, and the like;
e. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like;
f. expectorants, such as guaifenesin, ipecac, potassium iodide, terpin;
g. anti-diarrheals, such a loperamide, and the like;
h. $H_2$-antagonists, such as famotidine, ranitidine, and the like;
i. proton pump inhibitors, such as omeprazole, lansoprazole;
j. general nonselective CNS depressants, such as aliphatic alcohols, barbiturates and the like;
k. general nonselective CNS stimulants such as caffeine, nicotine, strychnine, picrotoxin, pentylenetetrazol and the like;
l. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like;
m. antiparkinsonism drugs such as levodopa, amantadine and the like;
n. opioid analgesics such as alfentanil, allylprodine, alphaprodine, anileridine, benzylmorphine, bezitramide, buprenoorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like. The opioid analgesic may be in the form of the free base, or in the form of a pharmaceutically acceptable salt, or in the form of a pharmaceutically acceptable complex;
o. analgesic-antipyretics such as salycilates, phenylbutazone, indomethacin, phenacetin and the like;
p. psychopharmacological drugs such as chlorpromazine, methotrimeprazine, haloperidol, clozapine, reserpine, imipramine, tranylcypromine, phenelzine, lithium and the like;
q. hypnotics, sedatives, antiepileptics, awakening agents;
r. vitamins and minerals;
s. amino acids and peptides;
t. compound like sildenafil citrate (Viagra etc);
u. proteins, hormones and peptides e.g., insulin, erythropoietin, etc.; and
v. antidiabetic drugs, e.g., metformin, glyburide and insulin secretart agent, insulin stimulators, fat metabolizers, carbohydrates metabolizers, insulin, cholesterol lowering agents like statins, etc.

Thus, a wafer formulation according to the invention comprising a pharmaceutical agent is an effective tool in the treatment of many diseases.

To incorporate a pharmaceutical agent into a wafer according to the invention, the pharmaceutical agent is dissolved in an aqueous solution and added to a gel formed by an aqueous mixture of a selected film-forming agent as previously described. The wafer-forming heating and cooling cycles are then applied to the admixture of the pharmaceutical agent and gel as described.

A method of administering a pharmaceutical agent to a mammal is also provided. The term "mammal" is used herein to encompass both human and non-human mammals such as domestic animals, livestock and wild animals. The method comprises the step of orally administering to the mammal a wafer in accordance with the invention comprising the pharmaceutical agent as described. The wafer dissolves in the aqueous environment of the oral cavity at a rate of at least about 2 mg/s, for example 3-5 mg/s, and on dissolution, the pharmaceutical agent is rapidly and effectively absorbed into the bloodstream to provide a plasma concentration that is at least comparable to the plasma concentration of the pharmaceutical agent that would be achieved by the intravenous injection thereof, and preferably the wafer provides an increased plasma concentration of the pharmaceutical agent.

Delivery of a pharmaceutical agent via an orally administrable wafer in accordance with the invention advantageously provides a mechanism for rapid access to the activity of the pharmaceutical agent in comparison with currently available orally administrable formulations. The wafer exhibits a very rapid rate of dissolution in an aqueous environment and, thus, provides expedited delivery of a pharmaceutical agent which translates into accelerated access to the activity of the pharmaceutical agent.

In addition, the present wafer formulation provides a rapidly dissolving oral dosage form comprising a defined quantity or dose of pharmaceutical agent not previously attainable. While prior batch extrusion methods for making film-like products cannot be used to generate dosage forms comprising a defined quantity of pharmaceutical agent, the heating/cooling cycling method of making the present wafer provides this capability. Generally, although the present method may be applied to produce a batch wafer product, the gel (film-forming agent in aqueous solution) may also be exposed to the heating/cooling cycles in plates having wells, for example, wherein each well contains a measured defined amount of pharmaceutical agent.

As will be appreciated by one of skill in the art, the present wafer formulation may comprise additional components. Such components may include one or more additives and/or excipients to optimize its use for oral administration. Examples of suitable additives include antimicrobial agents, plasticizing agents, flavoring agents, sulfur precipitating agents, saliva stimulating agents, cooling agents, surfactants, stabilizing agents, emulsifying agents, thickening agents, binding agents, coloring agents, sweeteners, fragrances, and the like. These additives/excipients are generally dissolved in an aqueous solution to form a solution of appropriate concentration with respect to the additive and then admixed with the film-forming gel prior to wafer formation.

The wafer formulation may include an anti-microbial agent such as one or more essential oils that confer antimicrobial properties. Preferably, the amount of a selected essential oil for use in the formulation is sufficient to provide antimicrobial efficacy. Generally, an oil such as thymol, methyl salicylate and eucalyptol may be present in an amount of about 0.01 to about 4 wt % of the formulation, preferably about 0.50 to about 3.0 wt % and even more preferably from about 0.70 to about 2.0 wt % of the formulation. Menthol may be added in an amount ranging from about 0.01 to about 15 wt % of the formulation, preferably about 2.0 about 10 wt % and even more preferably from about 3 to about 9 wt % of the formulation. The appropriate amount of a selected oil in the formulation can readily be determined by one of skill in the art. The amount of a selected oil in the formulation may exceed the foregoing amounts; however, the total oil content is such that it does not change the physical characteristics of the wafer formulation.

Saliva stimulating agents may be added to the wafer formulation according to the present invention. Saliva stimulating agents include food acids such as citric, lactic, malic, succinic, ascorbic, adipic, fumaric and tartaric acids. Preferred food acids are citric, malic and ascorbic acids. The amount of saliva stimulating agents suitable for inclusion in the present formulation may range from about 0.01 to about 12 wt %, preferably about 1 wt % to about 10 wt %.

Plasticizing agents may be included in the formulation to attain desired wafer flexibility and mold-releasing properties. Suitable plasticizing agents include, for example, triacetin, monoacetin and diacetin. Plasticizing agent may be added to the formulation in an amount ranging from about 0 to about 20 wt %, preferably about 0 to about 2 wt % of the formulation.

Cooling agents may be added to the formulation to increase boiling point of the gel and thereby prevent bubble formation. An example of a cooling agent that may be added to the formulation is monomenthyl succinate, in an amount ranging from about 0.001 to about 2.0 wt %, preferably about 0.2 to about 0.4 wt % of the formulation. A monomenthyl succinate-containing cooling agent is available from Mane, Inc. Other suitable cooling agents include WS3, WS23, Ultracool II and the like.

Another additive that may be included within the formulation is a surfactant. Mono- and di-glycerides of fatty acids and polyoxyethylene sorbitol esters, such as, Atmos 300 and Polysorbate 80, are examples of suitable surfactants for inclusion. The surfactant may be added in amounts ranging from about 0.5 to about 15 wt %, preferably about 1 to about 5 wt % of the formulation. Other suitable surfactants include pluronic acid, sodium lauryl sulfate, and the like.

Stabilizing agents such as xanthan gum, locust bean gum, guar gum and carrageenan, in amounts ranging from about 0 to about 10 wt %, preferably about 0.1 to about 2 wt % of the formulation, may be included in the formulation.

Emulsifying agents such as triethanolamine stearate, quaternary ammonium compounds, acacia, gelatin, lecithin, bentonite, veegum, and the like, may be included in the formulation in amounts ranging from about 0 to about 5 wt %, and preferably about 0.01 to about 0.7 wt % of the formulation.

Thickening agents such as methylcellulose, carboxyl methylcellulose, and the like, may be added to the formulation in amounts ranging from about 0 to about 20 wt %, and preferably about 0.01 to about 5 wt %.

Binding agents such as starch, may be included in the formulation in amounts ranging from about 0 to about 10 wt %, preferably about 0.01 to about 2 wt % of the film.

To render the formulation more desirable for oral administration, natural and/or artificial sweeteners may be included in the formulation. Suitable sweeteners include, e.g.:

a. water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

b. water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

c. dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenyl-glycine, L-aspartyl-2,5-dihydro-L-phenylalanine, L-aspartyl-L-(1-cyclohexyen)-alanine, and the like;

d. water-soluble sweeteners derived from naturally occurring water-soluble sweeteners, such as a chlorinated derivative of ordinary sugar (sucrose), known, for example, under the product description of sucralose; and e. protein based sweeteners such as thaumatoccous danielli (Thaumatin I and II).

In general, an effective amount of auxiliary sweetener is utilized to provide the level of sweetness desired for a particular composition, and this amount will vary with the sweetener selected. Generally, an amount of sweetener in the range of 0.01% to about 10% by weight of the formulation is appropriate, and will vary with the ability of the sweetener to sweeten and the desired level of sweetness. Of course, sweeteners need not be added to the formulation to render it orally administrable. In addition, the inclusion of sweeteners is independent from the inclusion of flavors in the formulation.

The flavorings that may be used in the formulation include both natural and artificial flavors. These flavorings may be chosen from synthetic flavor oils and flavoring aromatics and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. These flavorings may be used individually or in admixture. Commonly used flavors include mints such as peppermint, artificial vanilla, cinnamon derivatives, and various fruit flavors, whether employed individually or in admixture. Aldehydes and esters may be used to flavour as well. Examples include cinnamyl acetate, cinnamaldehyde, citral, diethylacetal, dihydrocarvyl acetate, eugenyl formate, p-methylanisole. Generally, any flavoring or food additive, such as those described in *Chemicals Used in Food Processing*, publication 1274 by the National Academy of Sciences, pages 63-258, may be used. Further examples of aldehyde flavorings include, but are not limited to, acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

The amount of flavoring employed is normally a matter of preference subject to such factors as flavor type, individual flavor, and strength desired. Thus, the amount may be varied in order to obtain the result desired in the final product. In general, amounts of about 0.1 to about 30 wt % may be used.

The formulation may also contain coloring agents or colorants. The coloring agents are used in amounts effective to produce the desired color. The coloring agents useful in the present invention include pigments such as titanium dioxide, which may be incorporated in amounts of up to about 5 wt %, and preferably less than about 1 wt %. Colorants can also include natural food colors and dyes suitable for food, drug and cosmetic applications. These colorants are known as FD&C dyes and lakes. The materials acceptable for use are preferably water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino) diphenyl-methylene]-[1-N-ethyl-N-p-sulfonium benzyl)-2,5-cyclo-hexadienimine]. A full recitation of all FD&C and D&C dyes and their corresponding chemical structures may be found in the *Kirk-Othmer Encyclopedia of Chemical Technology*, Volume 5, Pages 857-884.

The present invention advantageously provides an oral formulation that is rapidly dissolving on administration to provide rapid release of the pharmaceutical agent within the mouth and stomach. This renders the formulation particularly suitable to deliver pain medications such as medications used to treat acute breakthrough pain. In addition, the formulation may readily incorporate flavouring and sweetening agents to mask the taste of unpleasant pharmaceutical agents such as analgesic agents. Another advantage is provided in the efficiency of the method of making the present wafer formulation which involves a cost-effective technique of applying cycles of heating/cooling.

The above disclosure generally describes the present invention. It is believed that one of ordinary skill in the art may, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference in their entirety.

EXAMPLES

Although specific terms have been used in these examples, such terms are intended in a descriptive sense and not for purposes of limitation. Methods of molecular biology, biochemistry and chemistry referred to but not explicitly described in the disclosure and these examples are reported in the scientific literature and are well known to those skilled in the art.

Example 1

Preparation Method I

The following method was used to prepare a wafer. Examples of appropriate ingredient amounts are listed in Example 3.

a. The film-forming ingredients (e.g., xanthan gum, locust bean gum, carrageenan and pullulan) are mixed and hydrated in hot purified water to form a gel and stored in a refrigerator overnight at a temperature of approximately 4° C. to form preparation A;
b. The coloring agent(s) (selected food dye) and sweetener (sorbitol) are added to and dissolved in purified water to form preparation B;
c. Preparation B is added to preparation A and mixed well to form preparation C;
d. The flavoring agent and the oils (e.g. thymol, methyl salicylate, eucalyptol and menthol) are mixed to form preparation D;
e. The polysorbate 80 and Atmos 300 are added to preparation D and mixed well to form preparation E;
f. Preparation E is added to preparation C and mixed well to form preparation F; and
g. Fentanyl (100 micrograms) dissolved in water was added to the final mixture F and mixed well.

Preparation G is poured on a mold and cast to form a film of a desired thickness. The molds containing the film forming solutions were put on a conveyor belt and then passed through a special microwave chamber. Five microwave chambers were utilized for the quick film formation. Each microwave chamber had dimensions of about 14"×11"×9" and were programmed to heat the solution for 10 seconds. The conveyor belt speed was adjusted to move the molds slowly enough to complete the 10 seconds heating and drying cycle. Specifically the belt speed was adjusted to move the molds about 1 foot per 7 seconds (approximately 8 feet travel time) to provide sufficient time for the microwaves to complete one heating cycle. The microwaves were stationed about 18" away from each other. The whole chamber containing the microwave was designed to maintain the temperature of 37° C. with constant positive air flow. The wafers thus made were stored at room temperature. The whole cycle of making wafers of 1.5" long, 0.5 inch wide and 0.1 mm thick was about 90 seconds in total. The wafers were packaged and stored at room temperature.

Example 2

Preparation Method II

An alternative method for making a wafer as described herein includes the following steps. Examples of appropriate ingredient amounts are listed in Example 3.

a. dissolve copper gluconate, acesulfame K, aspartame, glycerin, sorbitol and dye in purified water to form an aqueous mixture;
b. mix pullulan, xanthan gum, locust bean gum and carrageenan together in powder form to form a powder mixture;
c. add the powder mixture from step B to the aqueous mixture from step A to form a hydrated polymer gel;
d. stir the hydrated polymer from step C at slow speed (about 50-100 RPM) overnight at room temperature;
e. mix and dissolve cooling agent, thymol, in menthol flavor oil;
f. add methyl salicylate, eucalyptol, Polysorbate 80 and Atmos 300 to the oil mixture from step E;
g. add the oil mixture from step F to the hydrated polymer gel from step D and mix until uniform;
h. add fentanyl (100 micrograms) to the mixture from step G (or the pharmaceutical agent of the choice) and mix well to form homogenous mixture;
i. cast the uniform mixture from step H on a suitable backing; and
j. expose the cast mixture to heating/cooling cycles as described in Example 1 using microwaves to form a wafer.

Example 3

Examples of Film Formulations

Examples of film formulations according to the present invention are set out in the following table.

| Ingredients | Example. 1 wt (mg) | Example 2 wt (mg) |
| --- | --- | --- |
| Xanthan Gum, Food Grade | 0.1000 | 0.10 |
| Locust Bean Gum, Clarified | 0.1150 | 0.10 |
| Polyvinyl Pyrrolidone | 0.1000 | 0.25 |
| Carrageenan | 1.0000 | 0.85 |
| PEG (mole wt 3000) | 1.0000 | 0.85 |
| Avicel | 0.2500 | 0.35 |
| Pullulan | 51.500 | 45.5 |
| Thymol NF | 0.4000 | 0.500 |
| Menthol NF | 0.5500 | 0.75 |
| Eucalyptol | 0.3500 | 0.25 |
| Methyl Salicylate USP | 0.5000 | 0.45 |
| Mint flavor | 8.5000 | 10.00 |
| Citric Acid | 0.7500 | |
| Copper gluconate | 1.1150 | 0.15 |
| Purified water, USP/EP | 23.584 | 31.94 |
| Sodium lauryl sulfate | 0.5000 | 0.500 |
| Aspartame | 6.500 | 5.00 |
| Cooling agent | 0.0750 | 0.05 |
| Sorbitol (crystalline) | 1.0000 | 1.000 |
| Glycerin | 1.0000 | .075 |
| Polysorbate 80 NF/EP | 0.5500 | 0.025 |
| Atmos 300 | 0.5500 | 0.55 |
| FD&C Green #3 | 0.0090 | 0.075 |
| D&C Yellow #10 | 0.0020 | 0.0100 |
| Total | | 100% |

Example 4

Characteristics of Wafer Formulation

A dissolution experiment was conducted to compare dissolution rate of a wafer prepared according to Example 1 with commercially available films prepared using the conventional extrusion process.

Fentanyl Wafer
Film Weight (average of 5 films)=107 mg+/−3 mg.
Thickness=15 micrometer The wafer was put in a clear 20 ml glass vial with 1 ml of cold water and vial was gently shaked (20 strokes/min) on rotating shaker. Dissolution time from solid to gel to complete solubilization was measured using a stop watch. The following observations were recorded at 5 second intervals:

| Time (sec) | Gel time | Complete Solubilization |
| --- | --- | --- |
| 0 | solid film | |
| 5 | thick gel | approx 20% soluble |
| 10 | sticky gel | approx 40-45% soluble |
| 15 | Still some gel | approx 70%+ soluble |
| 20 | little gel left | approx 90% soluble |
| 30 | no gel | complete soluble |

The experiment was repeated 5 times using 5 different wafer samples under identical conditions. The average complete dissolution time was calculated to be about 27 sec.

Listerine Film (Made by Wrigleys)

The same procedure was conducted on samples of Listerine film, manufactured by extrusion, to determine dissolution and gelling time of this film
Avg film sample wt=115 mg+/−5 mg
Thickness=20 micrometer

| Time (sec) | Gel time | Complete Solubilization |
| --- | --- | --- |
| 0 | solid film | |
| 5 | Solid | Approx 10% soluble |
| 10 | Solid | Approx 15-20% soluble |
| 15 | Solid | Approx 30%+ soluble |
| 20 | Thick gel | Approx 45% soluble |
| 25 | Thick gel | Approx 45% soluble |
| 30 | Thick gel | Approx 50% soluble |
| 40 | Thick gel | Approx 65% soluble |
| 50 | Thick gel | approx 80% soluble |
| 60 | Thick some gel | Approx 90% soluble |
| 75 sec | no gel | complete soluble |

The average dissolution time of 5 different Listerine film samples was determined to be approximately 70 sec.

Fruit Roll

The same procedure was conducted on samples of Listerine film, manufactured by extrusion, to determine dissolution and gelling time of this film.
Average film wt=330 mg+/−15 mg (same size as the listerine film)
Thickness=almost 4× the thickness of the listerine and fentanyl wafer (0.1 cm=100 μm)

| | | |
| --- | --- | --- |
| 0 | solid film | |
| 5 | thick gel | approx 1% soluble |
| 10 | sticky gel | approx 1% soluble |
| 15 | gel | approx 2%+ soluble |
| 20 | gel | approx 3% soluble |
| 25 | gel | approx 5% soluble |
| 30 | gel | approx 10% soluble |
| 40 | gel | approx 15% soluble |
| 50 | gel | approx 20% soluble |
| 60 | some gel | approx 25% soluble |
| 75 sec | some gel | approx 30% soluble |
| 100 sec | some gel | approx 45% soluble |
| 130 sec | some gel | approx 50% soluble |

-continued

| 150 sec | some gel | approx 50% soluble |
| 180 sec | some gel | approx 60% soluble |
| 240 sec | some gel | approx 70% soluble |
| 300 sec | some gel | approx 80% soluble |
| 360 sec | some gel | approx 90% soluble |
| 500 sec | some gel | approx 95% soluble |
| 700 | completely soluble | (water became viscous) |

The average dissolution time of 5 samples of the Fruit Roll-Up film was about 725-750 seconds.

Conclusion

A wafer made using the heating/cooling cycling method described herein exhibits a much quicker dissolution rate in comparison to comparable films made using the conventional extrusion methodology.

Example 4

Dog Clinical Data

To evaluate the safety and efficacy of an oral Fentanyl-containing wafer prepared using the ingredients described in Example 1 above, the wafer was delivered to 16 healthy dogs as described below. This study was conducted at the University of Guelph (Ontario Veterinary College) as an open label, randomized, crossover, and dose ranging comparative study of i.m. injection of 200 microgram Fentanyl vs three different doses (200, 400 and 800 micrograms) of oral Fentanyl wafer. The wafers used were 1.5-2 cm in diameter (circular shape) and approximately 0.05 mm thick The inclusion criteria were as follows:
Healthy dogs, no sign of any major illness
Normal findings during the screen visit
Male Female
Age 2-8 years
Weight <30 kgs
Dogs having any oral cavity disorder (for example, lesions, blisters, etc) were excluded from the study.

Screening Procedure Prior to Dosing:

Prior to the study, each dog underwent a general physical examination to establish general health status, including an electrocardiogram (six lead). Only those dogs with normal findings were considered healthy and permitted to enter the study.

Fentanyl Administration: Dogs were randomly assigned to treatment (study) groups; oral vs. intramuscular injection. All dogs were numbered in order to achieve proper randomization and to ensure that each dog received each treatment at different times. Each group was studied on separate days; the doses were scheduled at least 48-72 hrs apart to allow a complete wash out period. Treatment groups were as follows:
Treatment Group 1 (4 dogs)=Oral fentanyl (wafer containing 200 mg fentanyl)
Treatment Group 2 (4 dogs)=Oral fentanyl (wafer containing 400 mg fentanyl)
Treatment Group 3 (4 dogs)=Oral fentanyl (wafer containing 800 mg fentanyl)
Treatment Group 4 (4 dogs)=Intramuscular fentanyl injection (200 mg fentanyl)
All dogs received all four treatments on a separate occasion as per the randomization schedule An intravenous catheter (Insyte-W) was placed in a cephalic vein and a resting blood sample was drawn.

Drug levels were measured at time 0 (prior to drug administration), and at 10, 20, 30, 40, 50, 60, 75, 90, 120, 180, and 240 minutes following drug administration. Fentanyl blood concentrations (serum) were measured using the standardized ELISA method. Fentanyl ELISA Kits were purchased from either Bio-Quant Inc., San Diego, Calif., or from Neogen Corp, Lexington, Ky.

Assessment of Safety Precautions During the Study Period:

All safety measures were observed strictly during the study period. In case of respiratory depression, and abnormal vital signs, the study for that particular animal was terminated immediately. Pulse oxymetry was measured prior to and during the study at specified time points, and arterial blood pressure were also monitored via Doppler. The ECG was monitored throughout the study period at 0, 1, 3, 5 and 8 hrs Results:

The quantitative data analysis showed that administration of the fentanyl wafer was at least comparable to the i.m. administration of fentanyl as shown in FIG. 1.

The Cmax and Tmax for the absorption of fentanyl on administration of the 800 mcg wafer was determined to be approximately 6.93 ng in 5.6 min. The Cmax and Tmax for the absorption of fentanyl on administration of the 400 mcg wafer was determined to be approximately 4.83 ng in 5.7 min, and the Cmax and Tmax for the absorption of fentanyl on administration of the 200 mcg wafer was determined to be approximately 0.93 ng in 5.6 min. In contrast, the Cmax and Tmax for the absorption of fentanyl on administration of 200 mcg of fentanyl by i.m. injection was approximately 0.63 ng in 13.8 min.

There were no serious adverse events observed during the entire trial. All animals tolerated the oral wafer well. The heart rates, respiratory rates and blood pressure of each animal remained normal during the entire study period for all dosages. In addition, there were no signs that administration of the fentanyl wafer resulted in buccal mucosa damage, peeling of the mouth skin or burning/redness during the study.

What is claimed is:

1. An orally administrable wafer comprising at least about 30 to about 80 wt % pullulan, PEG in an amount of less than about 5 wt % and a pharmaceutical agent selected from the group consisting of morphine, heroin, hydromorphone, metophon, oxymorphone, levorphanol, codeine, hydrocodone, oxycodone, nalorphine, naloxone, naltrexone and fentanyl, wherein the wafer is prepared by dissolving the film forming agent in an aqueous solution to form a gel that is treated with a plurality of heating and cooling cycles for a total time period of no more than about 3 minutes and the wafer exhibits a dissolution rate of at least about 2 milligrams/sec in an aqueous environment and a $T_{max}$ of no more than about 10 minutes.

2. The wafer as defined in claim 1, additionally comprising one or more film forming agents selected from the group consisting of hydroxypropylmethyl cellulose, hydroxyethyl cellulose, hydroxypropyl cellulose, polyvinyl pyrrolidone, carboxymethyl cellulose, polyvinyl alcohol, sodium alginate, glycolide, polylactide, polyacrylic acid, methylmethacrylate copolymer, carboxyvinyl polymer, amylose, high amylose starch, hydroxypropylated high amylose starch, dextrin, pectin, chitin, chitosan, levan, elsinan and mixtures thereof.

3. The wafer as defined in claim 2, comprising the film forming agents polyvinyl alcohol and carrageenan.

4. The wafer as defined in claim 1, additionally comprising one or more compounds selected from the group consisting of: a plasticizing agent, a flavoring agent, a sulfur precipitating agent, a saliva stimulating agent, a cooling agent, a surfactant, a stabilizing agent, an emulsifying agent, a thickening agent, a binding agents, a coloring agent, a sweetener, and a fragrance.

5. The wafer as defined in claim 1, that exhibits a $T_{max}$ of the agent on administration of the wafer to a patient of less than about 7 minutes.

6. A method of preparing an orally administrable wafer comprising at least about 30 to about 80 wt % pullulan, PEG in an amount of less than about 5 wt % and a pharmaceutical agent selected from the group consisting of morphine, heroin, hydromorphone, metophon, oxymorphone, levorphanol, codeine, hydrocodone, xycodone, nalorphine, naloxone, naltrexone and fentanyl, wherein the wafer exhibits a dissolution rate of at least about 2 milligrams/sec in an aqueous environment and a $T_{max}$ of no more than about 10 minutes, the method comprising the steps of:
1) mixing the pullulan and PEG with an aqueous solution to form a gel, and mixing the pharmaceutical agent with the gel; and
2) exposing the gel to a plurality of cycles, each cycle comprising heating and cooling, to transform the gel into a wafer, wherein the total time period of the cycles is no more than about 3 minutes.

7. A method as defined in claim 6, wherein each cycle comprises a period of heating up to a temperature within the range of 60-90° C.

8. A method as defined in claim 6, wherein each cycle comprises a period of heating and a period of cooling, and each of said periods lasts about 5-15 s.

9. A method as defined in claim 6, comprising at least 3 cycles of heating and cooling.

10. A method as defined in claim 9, wherein the total time of the cycles is between about 1 and 2 minutes.

11. A method as defined in claim 6, wherein a measured amount of pharmaceutical agent is added to the gel to yield a wafer with a defined quantity of pharmaceutical agent therein.

12. A method as defined in claim 6, wherein the heating is achieved by exposure to microwaves.

13. A method of administering a pharmaceutical agent to a mammal comprising the step of orally administering to the mammal a wafer as defined in claim 1.

\* \* \* \* \*